United States Patent
Lindberg et al.

[11] Patent Number: 6,064,897
[45] Date of Patent: May 16, 2000

[54] SENSOR UTILIZING RAMAN SPECTROSCOPY FOR NON-INVASIVE MONITORING OF ANALYTES IN BIOLOGICAL FLUID AND METHOD OF USE

[75] Inventors: John M. Lindberg; Michael L. McGlashen, both of Grayslake, Ill.

[73] Assignee: Abbott Laboratories, Abbott Park, Ill.

[21] Appl. No.: 09/088,606

[22] Filed: Jun. 1, 1998

[51] Int. Cl.$^7$ ...................................................... A61B 5/00
[52] U.S. Cl. .......................... 600/316; 600/310; 600/322; 356/301
[58] Field of Search ..................................... 600/310, 316, 600/322, 323, 326, 473, 476; 356/39, 301; 250/339.01, 339.02, 339.07

[56] References Cited

U.S. PATENT DOCUMENTS

| | | |
|---|---|---|
| 5,221,957 | 6/1993 | Jannson et al. |
| 5,313,941 | 5/1994 | Braig et al. |
| 5,377,004 | 12/1994 | Owen et al. |
| 5,419,323 | 5/1995 | Kittrell et al. |
| 5,553,616 | 9/1996 | Ham et al. |
| 5,615,673 | 4/1997 | Berger et al. ............................ 600/326 |
| 5,754,289 | 5/1998 | Ozaki et al. ............................ 356/301 |

FOREIGN PATENT DOCUMENTS

| | | |
|---|---|---|
| 0751388 | 1/1997 | European Pat. Off. |
| 9210131 | 6/1992 | WIPO . |
| 9743611 | 11/1997 | WIPO . |

*Primary Examiner*—Eric F. Winakur
*Attorney, Agent, or Firm*—David L. Weinstein

[57] ABSTRACT

A noninvasive Raman sensor and an associated method of measuring at least one parameter of a sample, such as the presence or concentration of an analyte. The sensor includes (a) at least one source of light capable of irradiating the sample with substantially monochromatic light;

(b) a filtering module for filtering light scattered by the sample, that includes at least one bandpass filter capable of transmitting two different spectral windows; and (c) at least one detector.

The method includes (a) irradiating a sample with light from a source of substantially monochromatic light, (b) collecting light that is scattered by the sample, (c) analyzing the scattered light by passing the light through a filtering module that includes at least one bandpass filter that is transmissive for at least two spectral windows, and (d) detecting light that has been filtered by said filtering module.

The sample may be a biological fluid or other substance that has been obtained from the body or it may be a biological fluid or other substance located within a body part.

51 Claims, 7 Drawing Sheets

SENSOR UTILIZING RAMAN SPECTROSCOPY FOR NON-INVASIVE MONITORING OF ANALYTES IN BIOLOGICAL FLUID AND METHOD OF USE

BACKGROUND OF THE INVENTION

1. Field of the Invention

The present invention relates to devices and methods for measuring one or more parameters of a biological sample. More specifically, this invention relates to devices and methods for non-invasively detecting the presence or concentration of one or more analytes in vivo by Raman scattering.

2. Discussion of the Art

When light impinges on a sample, most of the scattered photons are elastically (or Rayleigh) scattered, meaning that they have the same frequency (or wavelength) as the incident radiation. A small fraction of the scattered light (less than one in a thousand incident photons) is inelastically (or Raman) scattered at frequencies that differ from the incident frequency by a value determined by the molecular vibrations of the sample. Raman scattering occurs at frequencies corresponding to the incident frequency plus or minus a molecular vibrational frequency as shown in equation (1):

$$\nu_{Raman} = \nu_o \pm \nu_{vib} \qquad (1)$$

where $\nu_{Raman}$ represents the Raman scattered frequency, $\nu_o$ represents the frequency of incident light (laser), and $\nu_{vib}$ represents a vibrational frequency of the molecule under study. A Raman spectrum is thus a plot of the intensity of scattered light as a function of frequency (or wavelength). By convention, Raman spectra are reported using wave number values (reciprocal centimeters) so that the abscissa is linear in energy.

Raman spectra have been used to characterize the structure and function of biological molecules, and in some cases, to identify and quantify the composition of complex, multicomponent samples. There are a number of recognized advantages to Raman spectroscopy as an analytical technique. It provides vibrational spectra that are rich in highly reproducible, detailed features, thereby providing the possibility of highly selective determinations. In comparing Raman and infrared (IR) spectroscopies, the Raman approach is advantageous for several reasons: (1) aqueous solutions present no special problems, (2) the low frequency region is easily obtained, and (3) optical components, such as windows, sample containers, and optical fibers can be made out of relatively inexpensive and readily available materials. Compared to absorption techniques, the Raman approach also permits considerable flexibility in the physical state of the sample. Because the selection rules for Raman scattering are different from those of IR absorbance, Raman scattering is complementary to IR measurements. In other words, vibrational modes that produce intense Raman bands may be invisible in the IR spectra.

Several inventors have recognized the potential for using Raman scattering as a non-invasive (NI) sensor. As defined herein, a "non-invasive" sensor is one that can be used without removing a sample from, or without inserting any instrumentation into, the tissues. U.S. Pat. No. 5,553,616 discloses the use of Raman scattering with excitation in the near infrared (780 nm) and an artificial neural network for measuring blood glucose. WO 92/10131 discusses the application of stimulated Raman spectroscopy for detecting the presence of glucose. Co-pending application Ser. No. 08/982,839, filed Dec. 2, 1997, incorporated herein by reference, describes a noninvasive glucose sensor that combines Raman measurements with complementary non-invasive techniques in order to enhance the sensitivity and selectivity of the measurement.

A major challenge for all of the NI Raman techniques to date has been to collect spectral information with sufficiently high signal-to-noise ratios to discriminate weak analyte signals from the underlying background. NI Raman measurements are hindered by a number of factors, some of which are listed below.

(a) Low Quantum Efficiency of Raman Scattering

The quantum efficiency of "normal" Raman scattering is low, thereby necessitating long integration times and high power densities to achieve acceptable signal-to-noise (S/N) ratios. Resonance and surface enhancement offer possibilities for extending the sensitivity and selectivity of Raman measurements and the intensity of some bands can be enhanced by as much as $10^6$ over the normal Raman spectrum. However, these enhancement mechanisms are not generally applicable to all analytes or to all samples, and relating band intensities to analyte concentrations under such circumstances requires careful calibration procedures.

(b) Fluorescence Background

In the visible region of the electromagnetic spectrum, indigenous tissue chromophores produce a broad and sloping fluorescence background that is difficult to subtract. Baselines encountered in Raman spectroscopy usually vary from one spectrum to the next even when samples are nominally the same. For in vivo measurements, both the intensity and the direction of the slope can be expected to change and Raman peaks are usually superimposed on slightly curved baselines. Fluorescence signals can be reduced by shifting to near-IR excitation, at the expense of reduced Raman intensity. Time resolved measurements, which discriminate against the fluorescence based on the differing temporal behaviors of the fluorescence and Raman signals, have also been used with some success.

(c) Spectral and Physiological Variables

In the ideal case, a NI Raman sensor would be highly sensitive for the parameter of interest (e.g., analyte concentration) while remaining insensitive to interfering analytes or physiological parameters. In practice, all of the NI Raman techniques described in the prior art are sensitive to one or more interfering "physiological" or "spectral" variables.

As used herein, the expression "physiological variables" describes physiological parameters, such as temperature or pulsatile blood flow, that can adversely affect the sensitivity or selectivity of a NI Raman measurement. Examples of several important physiological variables are listed in Table 1 below. As used herein, the expression "spectral variables" describes spectral features that arise either from poorly resolved analyte bands or from other interfering components in the sample. Several significant sources of spectral interference in biological samples, such as hemoglobin, albumin, cholesterol, urea, and fat, are listed in Table 2 below. Other tissue constituents that are present at lower concentrations or have lower scattering cross-sections may also contribute to an overall background signal that is difficult to subtract.

Referring again to Table 1 and Table 2, it is important to note that each of the physiological and spectral variables may fluctuate over time and each variable may oscillate at a different frequency. Methods that do not account for these oscillating variables will provide inaccurate results.

(d) Self-absorption

When a Raman band of the analyte falls within an absorption band of one of the sample components, much of the Raman scattered light may be absorbed by the sample, resulting in an underestimate of the analyte concentration. The degree of self-absorption is highly dependent upon the geometry of the measurement (i.e., orientation of the optics) and the sample composition.

(e) Instrument Size and Complexity

The vast majority of Raman scattering measurements in the prior art have been (and continue to be) performed in experimental research laboratories with the aim of elucidating the molecular structure, bonding, or reactivity of constituent molecules in a sample. Accordingly, the instruments used for most Raman measurements (i.e., dispersive Raman spectrometers) are designed to maximize experimental accuracy and flexibility. Most Raman spectrometers employ dispersive devices, such as Czerny-Turner spectrometers, to spread the scattered light spatially into a spectrum of different wavelength components. The Czerny-Turner spectrometer can be operated in two different modes, as described below.

First, the spectrometer can be used as a monochromator (i.e., selecting only one wavelength for analysis). For single wavelength detection, the spectral bandpass is determined by the entrance and exit slits of the monochromator and the resolution of the diffraction grating employed therein. The bandpass of the spectrometer can be adjusted to the spectral resolution required by the measurement (typically 0.5–10 cm−1). As used herein, the bandpass describes the full width of the band at half its maximal intensity (FWHM). The spectrometer diffraction grating is rotated (scanned), and a discrete detector, such as a photomultiplier tube, measures the intensity of the scattered light transmitted by the spectrometer.

Alternatively, the Czerny-Turner spectrometer can be used as a spectrograph, whereby a range of wavelengths is selected. In this case, an array detector, such as a photodiode array or an area detector, such as a charge coupled device (CCD), is placed at the back focal plane of the spectrometer (in place of the exit slit). Spectral resolution is controlled by the entrance slit of the spectrometer and the groove density of the diffraction grating. The scattered intensity is recorded over a preselected wavelength range, thereby providing a multi-channel advantage over the scanning method described above. However, the grating may require movement and recalibration, however, if the wavelength range of the measurement is changed.

Although Czerny-Turner spectrometers provide highly accurate and adjustable selection of the wavelength and spectral bandpass, the transmissivity of these devices is low. Thus, the time required to obtain a complete Raman spectrum is unacceptably long for use as a NI sensor. Although the instrument can provide measurements of discrete spectral features in the scanning mode, only one wavelength may be sampled at any given time. Further, valuable time is lost while the grating is moved to interrogate different portions of the Raman spectrum. The mechanical motion required by this system can also cause repositioning errors, thereby increasing uncertainty of accuracy of wavelength. In general, devices employing Czerny-Turner spectrometers are too large, complicated, and expensive for field use by inexperienced operators.

Recent progress in the area of electronically tunable filters offers some hope for reducing the size of Raman spectral filtering devices. The acousto-optic tunable filters (AOTFs) can provide broad tunability and multiplex operation. However, the spectral bandpass of an AOTF is too large for most Raman measurements. A liquid crystal tunable filter (LCTF) can provide a narrower spectral bandpass, but such a filter is limited to the detection of one wavelength at a time. The maximum transmissivity of a LCTF (approximately 16%) also limits the sensitivity of this device.

Fixed filters are a cost-effective alternative to the dispersive devices and electronically tunable filters described above. Although fixed filters lack the flexibility of the variable wavelength selective devices, they are robust, compact, and much less expensive than dispersive instruments or electronically tunable filters. Their high transmissivities (>80%) reduce signal acquisition times, and their spectral properties (e.g., $\lambda_{max}$, $\Delta\nu_{1/2}$, rejection ratio) are selected at the factory, thereby eliminating the need for electronic controllers and moving parts.

Fixed filters are designed to attenuate all but the desired wavelengths of radiation. For example, they can be used to pass a band of wavelengths (bandpass filters) or to block wavelengths longer or shorter than some desired value (cutoff filters). Bandpass filters are characterized by a plot of their spectral transmittance vs. wavelength, as shown in FIG. 1(a), which exhibits a characteristic wavelength of maximum transmission ($\lambda_{max}$) and a bandpass ($\Delta\nu_{1/2}$) measured as the full width at half maximum. Most bandpass filters are made with alternating layers of high-refractive and low-refractive index dielectrics. Multilayer interference filters can achieve quite narrow FWHM bandpass (less than 10 $cm^{-1}$) values with high peak transmittances (greater than 50%) from the ultraviolet to the infrared.

Cutoff filters attenuate radiation at wavelengths shorter than a given cutoff wavelength (short-wavelength cutoff) or radiation at longer wavelengths than a given cutoff wavelength (long-wavelength cutoff). The transmittance of a short-wavelength cutoff filter is illustrated in FIG. 1(b). Dichroic mirrors are wavelength selective beam splitters with transmission characteristics that are similar to cutoff filters. Longpass dichroic mirrors transmit radiation at wavelengths that are longer than a given cutoff wavelength and reflect radiation at shorter wavelengths.

Holographic filters have the sharp cut-off characteristics of the multilayer dielectric filters described above and high transmissivities (80–90%). The transmission curves of holographic filters are featureless, as opposed to the transmission curves of dielectrics, which have numerous features due to multiple layer interferences.

EP 0781990 to Ozaki et al., hereinafter Ozaki '990, describes a Raman filtering device for urinalysis comprising multiple bandpass filters or a combination of cutoff filters for selecting particular wavelengths of Raman scattered light. For measurements at multiple wavelengths, Ozaki '990 provides a filter wheel, which can be rotated to provide several different filters in succession.

Ozaki '990 is inappropriate for in vivo measurements where spectral and physiological variables fluctuate over time. In particular, the device of Ozaki '990 is incapable of collecting Raman signals at two wavelengths simultaneously. Changing filters by spinning the filter wheel also causes slight changes in alignment, which can alter collection efficiency, thereby providing erroneous measurements of in vivo analyte concentrations.

Despite the wide variety of instrumental configurations used to date, NI Raman sensors are not yet commercially available. Accordingly, there is a need for a compact, rugged, inexpensive, sensitive, and selective Raman sensor that measures in vivo analyte concentrations in the presence of fluctuating physiological and spectral variables.

SUMMARY OF THE INVENTION

The present invention provides a noninvasive Raman sensor and an associated method of measuring at least one parameter of a sample, such as the presence or concentration of an analyte. In one aspect, the invention provides an apparatus comprising:

(a) at least one source of light capable of irradiating said sample with substantially monochromatic light;

(b) a filtering module for filtering light scattered by said sample, said filtering module comprising at least one bandpass filter, said at least one bandpass filter capable of transmitting two different spectral windows; and (c) at least one detector.

In another aspect, the invention provides a method that employs the foregoing apparatus. The sample may be a biological fluid or other substance that has been obtained from the body or it may be a biological fluid or other substance located within a body part.

A key feature of the present invention involves measuring the intensity of light scattered by a sample as a function of at least two different spectral windows. As used herein, a "spectral window" is a configuration of the Raman sensor that is defined by the following three parameters:

(1) a wavelength of light incident upon the sample, $\lambda_o$, (2) a wavelength of maximum intensity, $\lambda_{max}$, transmitted by the filtering module, and (3) a spectral bandpass, $\Delta v_{1/2}$, transmitted by the filtering module.

For example, in one embodiment the intensity of light scattered by a sample may be recorded using two different values of $\lambda_{max}$. Such a measurement can be represented symbolically as follows:

$$I_1 = I(\lambda_{o,1}, \lambda_{max,1}, \Delta v_{1/2,1}) \text{ and } I_2 = I(\lambda_{o,1}, \lambda_{max,2}, \Delta v_{1/2,1})$$

where $I_1$ and $I_2$ represent the intensities of light scattered by a sample recorded for first and second spectral windows, respectively, $\lambda_{o,1}$ represents the incident light wavelength, $\lambda_{max,1}$ and $\lambda_{max,2}$ represent wavelengths of maximum transmission for the first and second spectral windows, respectively, and $\Delta v_{1/2,1}$ represents the spectral bandpass for the first and second spectral windows. As described above, measurements of $I_1$ and $I_2$ might, for example, be used to selectively monitor different constituents present in the sample.

In another embodiment, the intensity of light scattered by a sample may be recorded using two different values of $\lambda_o$. Such a measurement can be represented symbolically as follows:

$$I_1 = I(\lambda_{o,1}, \lambda_{max,1}, \Delta v_{1/2,1}) \text{ and } I_2 = I(\lambda_{o,2}, \lambda_{max,1}, \Delta v_{1/2,1})$$

where $I_1$ and $I_2$ represent the scattered light intensities recorded for first and second spectral windows, respectively, $\lambda_{o,1}$ and $\lambda_{o,2}$ represent the incident light wavelengths for first and second spectral windows, respectively, $\lambda_{max,1}$ represents the wavelength of maximum transmission for the first and second spectral windows, and $\Delta v_{1/2,1}$ represents the spectral bandpass for the first and second spectral windows. As described above, measurements of $I_1$ and $I_2$ might, for example, be used to remove interferences due to sample fluorescence.

In another embodiment, the intensity of light scattered by a sample may be recorded using different values of $\Delta v_{1/2}$. Such a measurement can be represented symbolically as follows:

$$I_1 = I(\lambda_{o,1}, \lambda_{max,1}, \Delta v_{1/2,1}) \text{ and } I_2 = I(\lambda_{o,2}, \lambda_{max,1}, \Delta v_{1/2,2})$$

As described above, measurements of $I_1$ and $I_2$ might, for example, be used to remove interferences due to spectral variables.

In the embodiments described above, the intensity of scattered light is recorded as a function of at least two different spectral windows in order to provide a measurement that is indicative of, for example, the presence or concentration of one or more analytes in the sample, a disease state of the sample, or some other property of the sample that is determinable by Raman scattering measurements. The devices and methods of the present invention are particularly well suited for non-invasively measuring analyte concentrations in vivo in the presence of fluctuating physiological and spectral variables.

In a preferred embodiment, the intensity of scattered light is recorded as a function of least two different spectral windows simultaneously. In a particularly preferred embodiment, the intensity of scattered light is recorded for at least two spectral windows without mechanical motion. In an even more preferred embodiment, the filtering module used for such measurements has high spectral resolution (no greater than 7 cm$^{-1}$ spectral bandpass) and a transmissivity greater than about 20%, preferably greater than about 50%, more preferably greater than about 80%. In a most preferred embodiment, the filtering module comprises two or more bandpass filters, wherein at least two of the bandpass filters have substantially different values of $\lambda_{max}$ (wavelength of maximum transmission) or $\Delta v_{1/2}$ (spectral bandpass).

In another embodiment, the present invention provides a Raman scattered light measuring apparatus comprising:

(a) a source of substantially monochromatic light;

(b) a filtering module comprising at least two bandpass filters, and (c) a detector wherein a first bandpass filter includes a vibration wave number that is specific to a first analyte in its transmission band and a second bandpass filter that does not include a vibration wave number that is specific to the first analyte in its transmission band.

In another aspect of the invention, the present invention comprises a method for making Raman scattering measurements comprising the steps of:

(a) irradiating a sample with light from at least one source of substantially monochromatic light, (b) collecting light that is scattered by said sample, (c) analyzing said scattered light by passing the light through a filtering module, wherein said filtering module comprises at least one bandpass filter, and wherein said at least one bandpass filter is transmissive for at least two spectral windows, and (d) detecting light that has been filtered by said filtering module.

The sample may be a biological fluid or other substance that has been obtained from the body or it may be a biological fluid or other substance located within a body part.

This invention provides several advantages with respect to the prior art. First, the invention results in lower cost relative to a spectrometer. Second, the invention can be made to specific for one or more analytes.

DETAILED DESCRIPTION

Figure 1A:
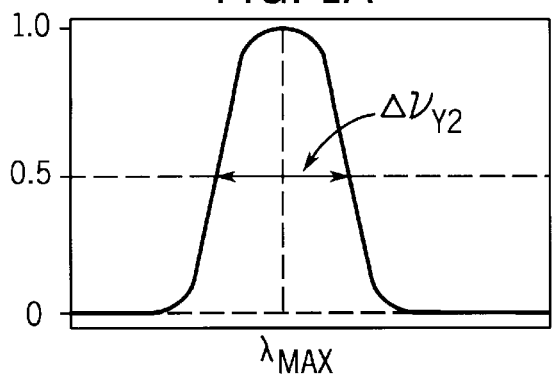
FIG. 1A is a graph illustrating the transmission characteristics of a bandpass filter.
Figure 1B:
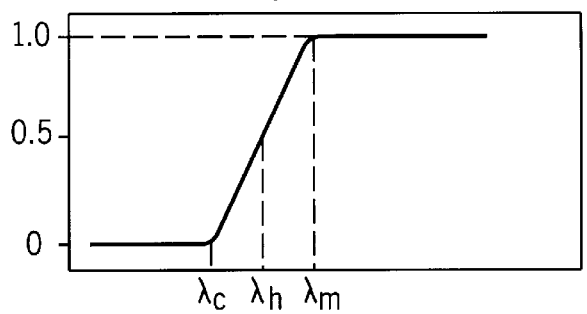
FIG. 1B is a graph illustrating the transmission characteristics of a cutoff filter.

The design requirements for non-invasive (NI) sensors are quite different from those of the experimental Raman devices described previously. NI sensors must be robust, that is, they must provide accurate results despite variations in environmental conditions and interfering spectral and physiological variables. They must also provide high sensitivity (high transmissivity), thereby providing useful signal-to-noise ratios with a minimum acquisition time. In order to be commercially useful, they must be inexpensive and provide accurate measurements when used by inexperienced operators in the field. In this invention, the foregoing criteria are met in a Raman sensor comprising at least one fixed filter for measuring the intensity of scattered light as a function of at least two different spectral windows.

There are numerous advantages in selecting a plurality of wavelengths for the foregoing plurality of spectral windows. One advantage relates to monitoring a plurality of constituents in a sample. Bandpass filters may be selected to monitor specific vibrational signatures of the analyte(s) of interest while other filters may be used to select light that is indicative of other constituents of the sample or to monitor background signals for subsequent subtraction. In the latter case, the filters can be optimized to maximize the signal from the analyte while minimizing sources of interfering noise.

Another advantage relates to correcting for matrix effects. Vibrational spectroscopy is a sensitive probe of molecular conformation. For glucose measurements, the vibrational bands in the Raman spectra that result from the C—O and H—O—H stretching vibrations are particularly important. The vibrational frequencies and intensities of these bands depend upon the hydrogen bonding characteristics of the sample. In turn, hydrogen bonding is strongly dependent upon electrolyte concentrations, pH, and temperature. As a result, these parameters can cause variability in measurements involving vibrational modes that are sensitive to hydrogen bonding. By measuring the intensity of scattered light at a plurality of wavelengths, vibrational spectra can be "self-corrected", that is, certain vibrational bands that arise from electrolytes can be used to correct for the impact of the electrolyte concentration on other bands (e.g., H-bonding bands).

Another advantage relates to correcting for self-absorption and optical pathlength. A change in temperature can affect the near infrared (NIR) absorption spectrum by altering the intensities as well as the frequencies of the dominant water absorption bands. A temperature change will also modify the refractive index of the sample, which, in turn, will alter the scattering properties of the sample. The effective optical path length will change as a result of the aforementioned change in scattering properties. The temperature dependence of the NIR water spectrum complicates glucose measurements by providing a variable absorption, which must be accounted for in order to provide accurate glucose concentration measurements.

The use of an internal standard in Raman measurements can be used to correct for self-absorption. When the sample absorbance is approximately the same at the wavelengths of the analyte and the internal standard Raman bands, internal standardization corrects for absorption of the incident and Raman scattered radiation.

Still another advantage relates to optimization of alignment. The setup of Raman instruments requires careful optimization of the physical positions of the various optical components. In one embodiment, the filtering module of the present invention is configured according to a first spectral window wherein the signal from a high intensity band is transmitted to the detector for alignment purposes. After the optical alignment is complete, the filtering module can be left unaltered during acquisition of the weaker analyte signal(s). For continuous monitoring, or for measurements over a long period of time, it may be advantageous to optimize the optical alignment intermittently during the measurement. Alternatively, an alignment and calibration routine may be used after the measurement to normalize for signal variations for alignment drift.

Figure 2B:
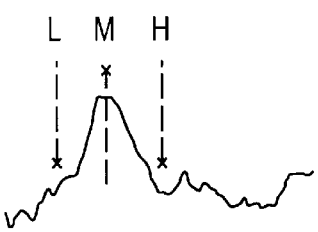
FIG. 2 is a graph illustrating the effects of background noise and fluorescence on Raman bands.
Figure 2A:
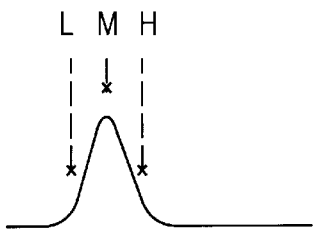
Figure 2C:
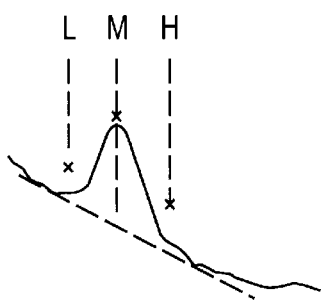

Another advantage relates to correcting for fluorescence background. FIG. 2 shows the effect of a baseline variations on a typical Raman band where curve (a) denotes a high signal-to-noise (S/N) reference band, curve (b) denotes a band the same size as that shown in curve (a) but contaminated with noise and superimposed on a variable, non-sloping background, and curve (c) denotes a band the same size as that shown in curve (a) but contaminated with noise and superimposed on a variable, sloping background. Labels L and H denote the low- and high-frequency sides of the Raman band, while label M indicates the midpoint of the Raman band. For methods that monitor the signal intensity only at the midpoint of the Raman band, changes in the intensity and slope of the fluorescent background will deleteriously affect the sensitivity of the measurement. In one embodiment, the present invention comprises monitoring the scattered light intensity at wavelengths corresponding to labels L, M, and H. Appropriate background subtraction measures may be employed to eliminate the effects due to changes in the fluorescence background There are numerous advantages in selecting a plurality of bandpass values for the plurality of spectral windows. One advantage relates to matching the filter bandwidth to the analyte bandwidth. For analytical purposes, it is important to sample as much of the analyte signal as possible while excluding background signals. Thus, the bandwidth of a filter that is designed to select the Raman scattered light from a particular band in the Raman spectrum should ideally be matched to the bandwidth of the analyte band. The selection of a filter bandwidth may also be modified by other factors, including spectral crowding in the region of the analyte bands. For example, when it is known that vibrational bands from other components of the sample encroach upon the spectral region of the analyte, a filter having a narrower bandpass may be selected to eliminate these perturbing signals. In one embodiment of the present invention, a filtering module comprising a plurality of filters having different values of $\Delta v_{1/2}$ are provided for filtering light that is scattered by the sample.

The following non-limiting examples illustrate the present invention.

EXAMPLE 1

Figure 3:
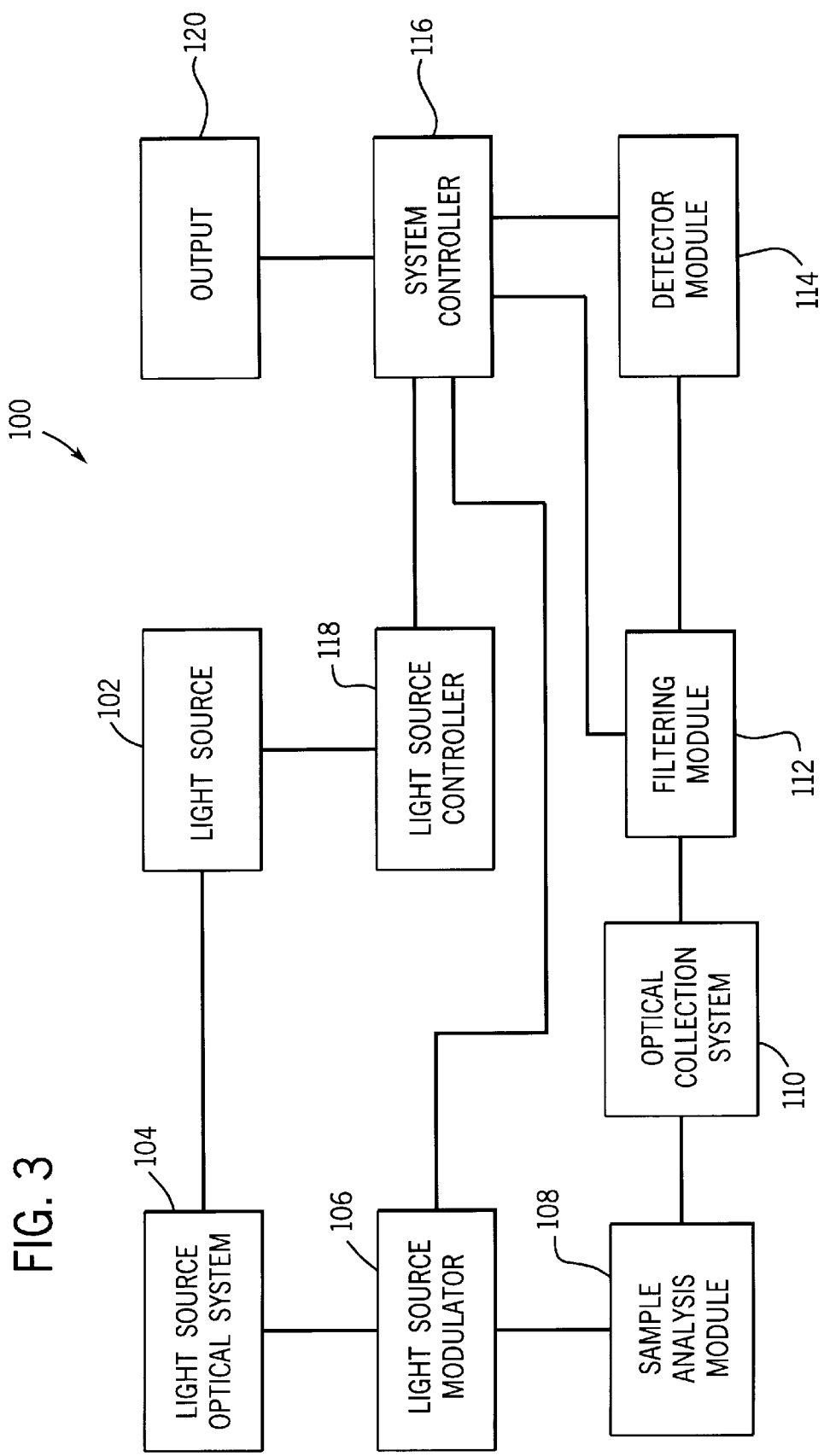
FIG. 3 is a schematic (block) diagram of a compact, robust Raman sensor according to one embodiment of the present invention.

FIG. 3 is a schematic (block) diagram of a Raman sensor 100 according to one embodiment of the present invention. Light from a substantially monochromatic light source 102, such as diode laser, is coupled to a light source optical system 104, which is adapted for illuminating the sample. The light source 102 can comprise at least two sources of light for irradiating a sample or a body part. Each of the two sources of light may preferably use substantially monochromatic light of different wavelength. The light source optical system 104 may comprise, for example, an optical fiber bundle, a series of lenses, or the like. For measurements requiring a modulated light source, a light source modulator 106, may be used in conjunction with, or as part of, the light source optical system 104. The light source modulator 106 modulates the intensity, wavelength, bandwidth, phase, or polarization state of the light.

A sample analysis module 108 provides an interface between the sample and the Raman sensor. The sample analysis module 108 is disposed near the surface of the sample, preferably in physical contact with the sample, and is adapted to optimize the efficiency of collection of scattered light therefrom. An optical collection system 110 collects the light that is scattered by the sample and transmits it to a filtering module 112. The optical collection system 110 may comprise, for example, an optical fiber bundle, a series of lenses, an optical imaging device, or the like.

The filtering module 112, which selectively transmits light that is scattered by the sample, provides at least one bandpass filter, wherein the at least one bandpass filter transmits at least two spectral windows of the scattered light to a detector module 114.

The detector module 114 comprises a detector, such as a photomultiplier, a photodiode detector, a CCD, or the like. For a wavelength modulated light source, an intensity modulated light source, or a polarization modulated light source, the detector module 114 may include a lock-in amplifier to detect the scattered light.

A system controller 116 is adapted to control the operation of a light source controller 118, the light source modulator 106, the filtering module 112, and the detector module 114. Under certain circumstances, the light source controller 118, the light source modulator 106, or the filtering module 112, may operate independently of the system controller 116. The system controller 116 may comprise an on-board central processor, data-processing hardware and software, and associated electronics. The results of the measurement are communicated to the user via an output 120, which may comprise, for example, a liquid crystal display, an audio readout, or the like.

Measurements that are of particular interest include those of blood constituents, such as glucose, hematocrit, and hemoglobin.

EXAMPLE 2

Figure 4:
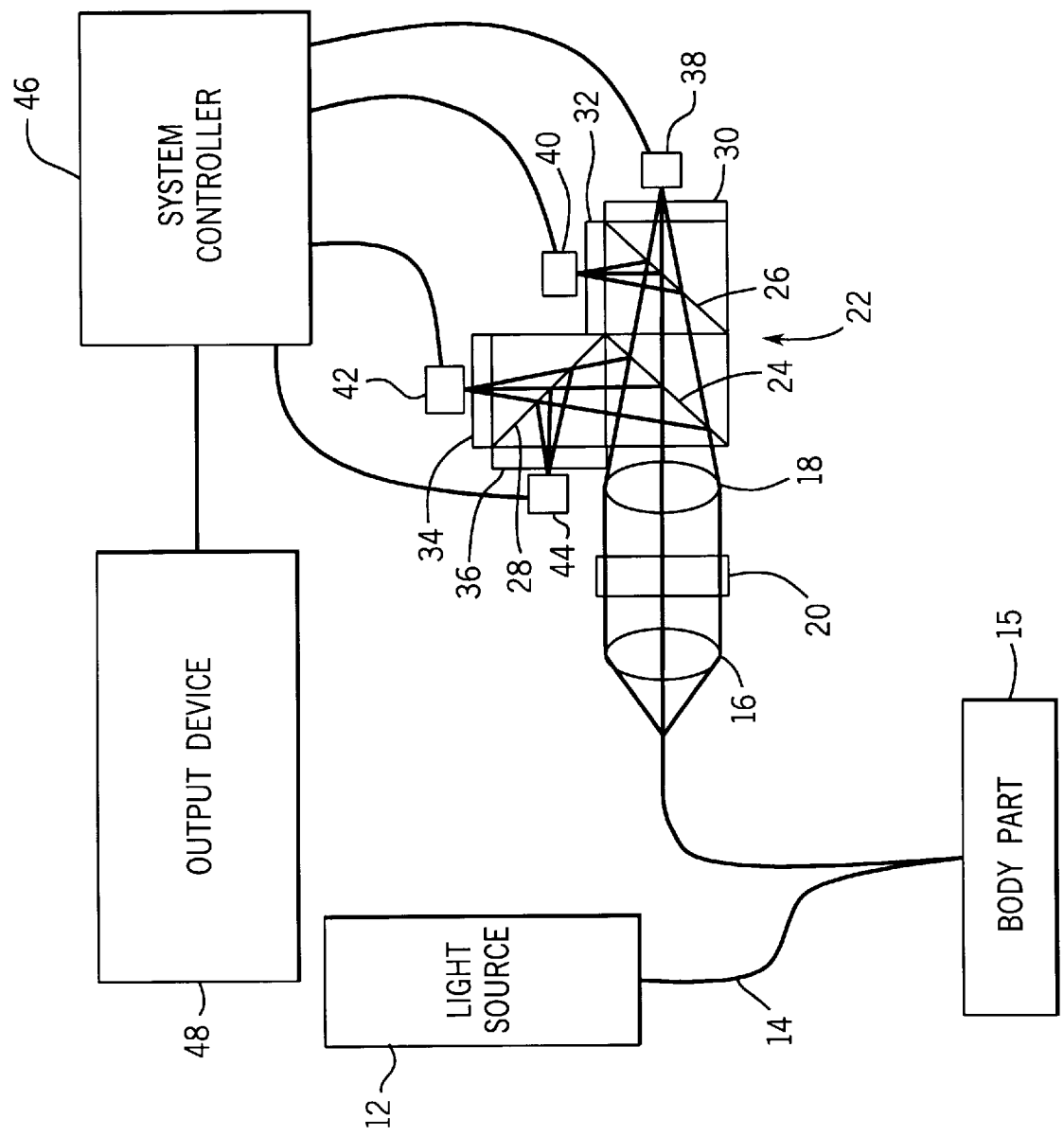
FIG. 4 is a schematic diagram of a compact, robust Raman sensor according to one embodiment of the present invention.

FIG. 4 is a schematic diagram expressing the structure of FIG. 3 with commercially available optical elements and components. A substantially monochromatic light source 12, such as a diode laser, is coupled to bifurcated optical fiber probe 14, which is adapted for illuminating a sample or body part 15. As used herein, the expression "body part" is intended to include skin, earlobe, finger, lip, forehead, tongue, etc. Because the principles within the scope of this invention can be adapted by those skilled in the art for in vitro measurement of hematocrit and other blood constituents, the expression "body part" is intended to include various in vitro blood containers such as tubes and cuvettes. The body part 15 is preferably held by a fixture to insure accuracy of measurement. The optical collection system consists of lenses 16 and 18 and a notch filter 20, the purpose of which is to reject Rayleigh scattered light. Light that is scattered by the sample is focused by the optical collection system onto a filtering module 22. The filtering module 22 comprises beam splitters 24, 26, and 28, which split the scattered light into multiple components. Bandpass filters 30, 32, 34, and 36 selectively transmit bands of radiation that are centered on preselected wavelengths. For example, bandpass filters 30, 32, 34, and 36 may selectively transmit light having four different values of $\lambda_{max}$.

Light that is selectively transmitted by filters 30, 32, 34, and 36 is detected by detectors 38, 40, 42, and 44, which can comprise, for example, photomultipliers, photodiode detectors, CCDs, or the like. For a modulated light source, a lock-in amplifier can be used to detect the scattered light at one or more preselected modulation frequencies.

System controller 46 is adapted to control the operation of and collect data from detectors 38, 40, 42, and 44. Output device 48 consists of a liquid crystal display. An on-board central processor, data-processing hardware and software, and associated electronics are also provided with this embodiment.

EXAMPLE 3

Figure 5:
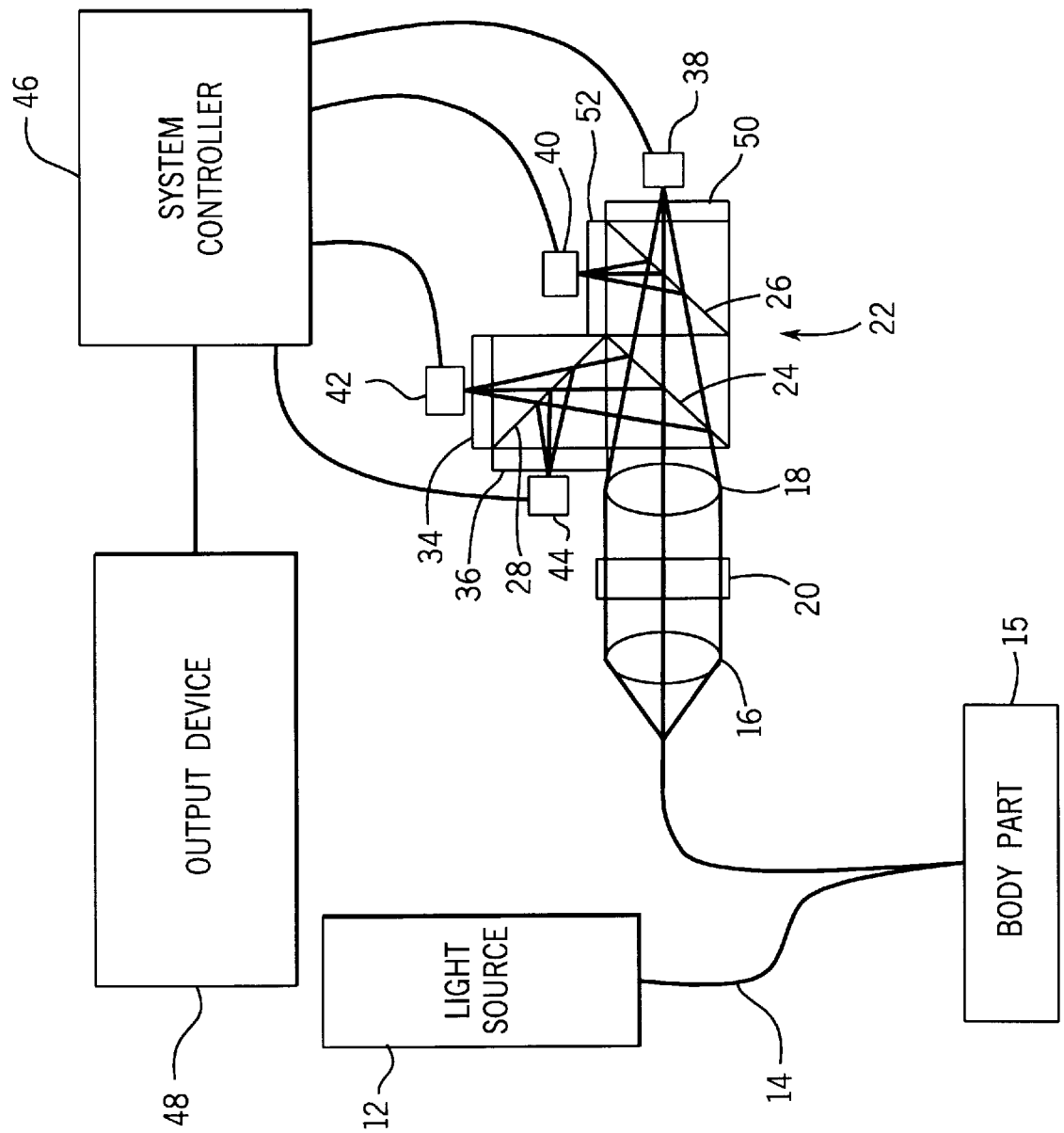
FIG. 5 is a schematic diagram of a compact, robust Raman sensor according to one embodiment of the present invention.

FIG. 5 shows an alternative embodiment of the Raman sensor shown in FIG. 4. In FIG. 5, components having the same reference numerals as components in FIG. 4 have the same identities and functions as have those components in FIG. 4. The embodiment shown in FIG. 5 comprises several additional components.

Figure 6:
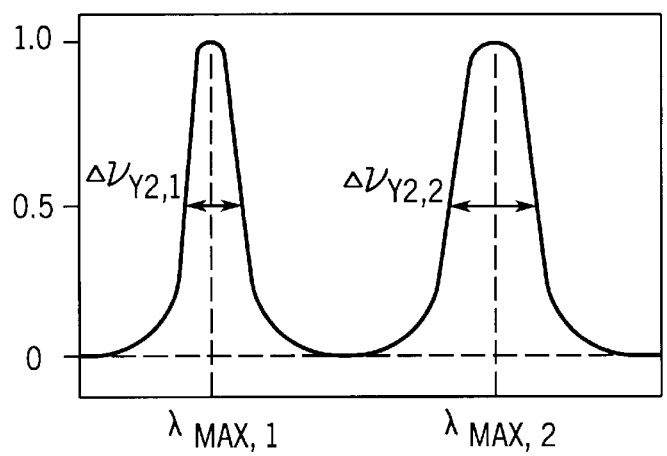
FIG. 6 is a graph illustrating the transmission characteristics of a bandpass filter having two values of $\lambda_{max}$.

A filter 50 can selectively transmit two or more bands of radiation characterized by different values of $\lambda_{max}$ (e.g., $\lambda_{max,1}$ and $\lambda_{max,2}$), as illustrated in FIG. 6. Two or more bands selected by a filter 50 may, for example, be used to monitor signals arising from one or more analytes in the sample. Prior to constructing the sensor, a principal components analysis, a factor analysis, a genetic algorithm, or a similar method may be used to select one or more wavelengths that are optimal for monitoring analytes in the sample while minimizing signals from interfering analytes or background noise. A filter 52 can selectively transmit one or more bands of radiation indicative of, for example, one or more spectral variables or background noise.

EXAMPLE 4

Figure 7:
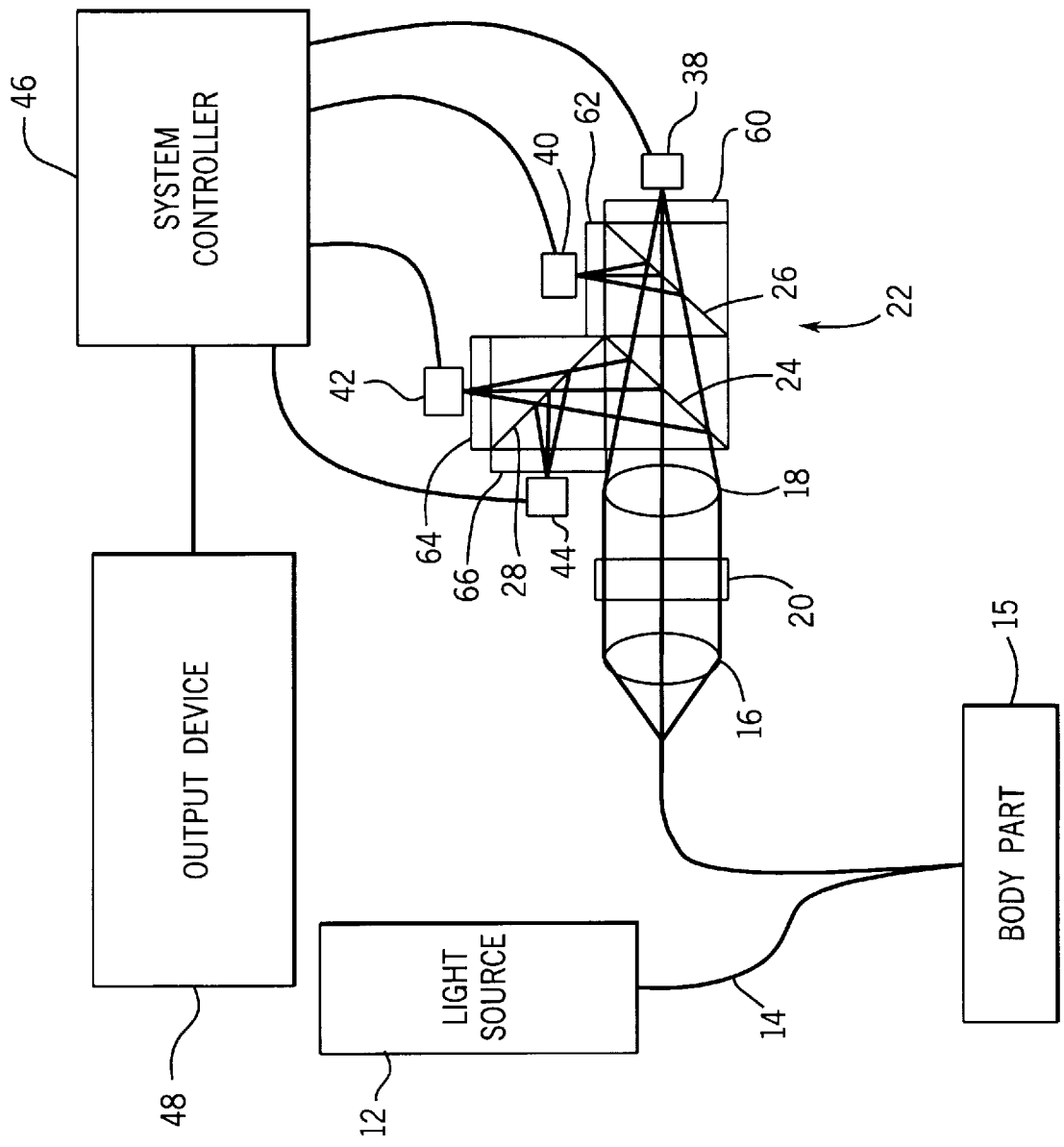
FIG. 7 is a schematic diagram of a compact, robust Raman sensor according to one embodiment of the present invention.

FIG. 7 shows an alternative embodiment of the Raman sensor shown in FIG. 4. In FIG. 7, components having the same reference numerals as components in FIG. 4 have the same identities and descriptions as have those components in FIG. 4. The embodiment shown in FIG. 7 comprises several additional components.

It is known that holographic and dielectric filters are angle-tunable over a small wavelength range. In other words, the value of $\lambda_{max}$ transmitted by the filter changes as the angle between the incident light ray and the optical axis of the filter changes. This feature may be used to advantage in the present invention where it is desirable to obtain scattering measurements at several closely spaced wavelengths as shown, for example, in positions L, M, and H of FIG. 2.

A commercial advantage of such an approach can be realized in that a single filter design having a nominal $\lambda_{max}$ value can be used to selectively transmit bands of light having two or more different effective $\lambda_{max}$ values. Thus, economies of scale can be achieved in the design and manufacture of filters for the present invention. For example, referring again to FIG. 7, filters 60, 62, 64, and 66 comprise four identical filters that are placed at different angles (angles not shown) with respect to the transmission axis of the filtering module. Thus, the filters 60, 62, 64, and 66 transmit four different filter passbands having three different effective $\lambda_{max}$ values. By means of arrangements such as this, the filtering module is capable of selecting two or more spectral windows without requiring mechanical movement of the filters. Moreover, by means of arrangements such as this, the filtering module is capable of selecting two or more spectral windows simultaneously.

EXAMPLE 5

Figure 8:
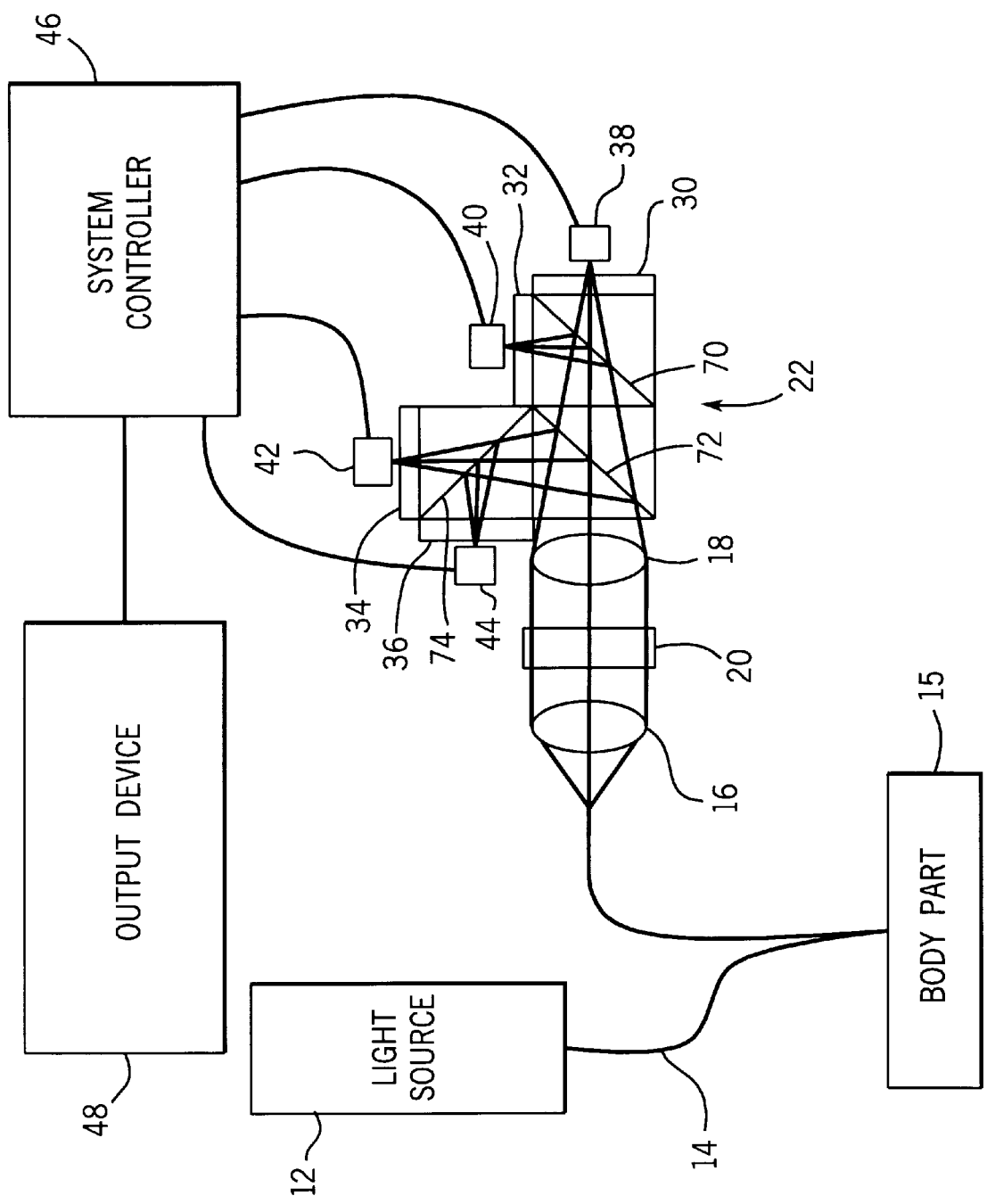
FIG. 8 is a schematic diagram of a compact, robust Raman sensor according to one embodiment of the present invention.

FIG. 8 shows an alternative embodiment of the Raman sensor shown in FIG. 4. In FIG. 8, components having the same reference numerals as components in FIG. 4 have the same identities and descriptions as have those components in FIG. 4. The embodiment shown in FIG. 8 comprises several additional components.

Dichroic mirrors 70, 72, and 74 have different wavelength cutoff values and split the light entering the filtering module into different wavelength ranges. An advantage of dichroic mirrors over the beam splitters shown in FIG. 4 is that the reflectivities and transmissivities of dichroic mirrors are much higher than the 50% theoretical maximum achieved by cubic beam splitters.

EXAMPLE 6

Figure 9:
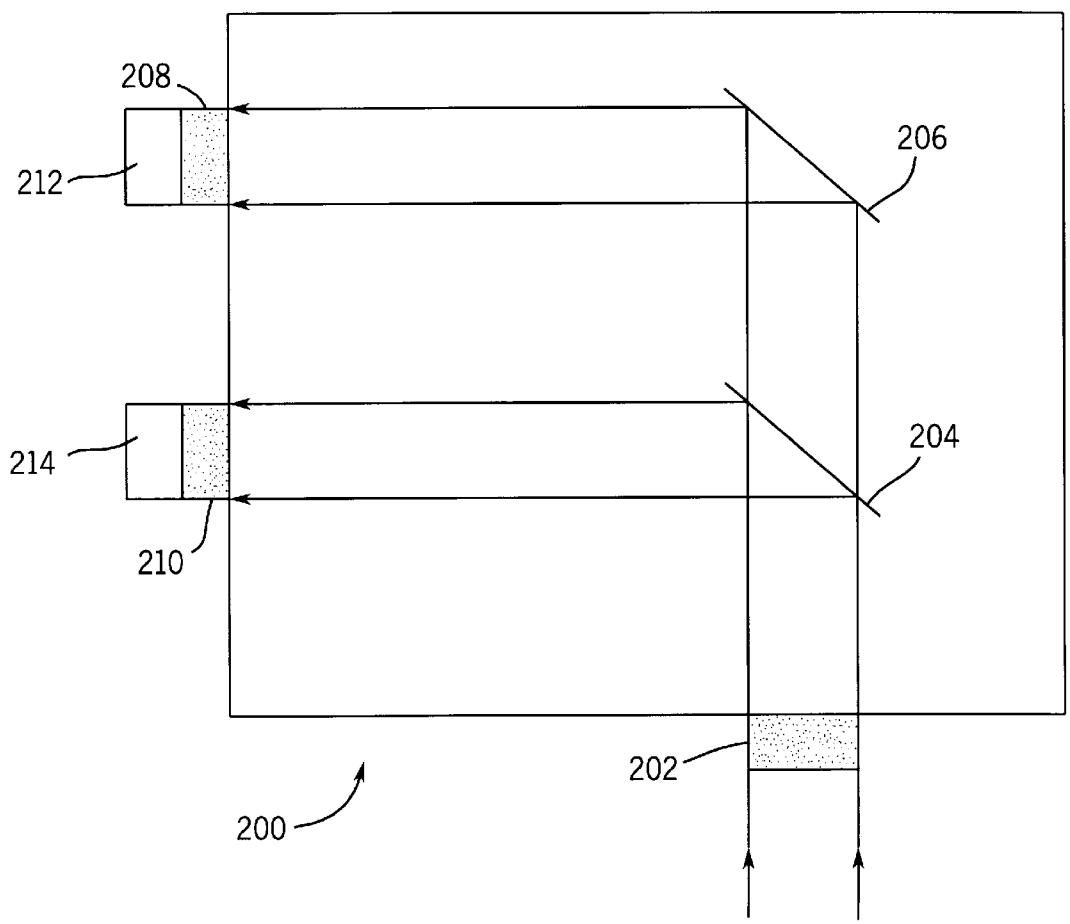
FIG. 9 is a schematic diagram of a Raman imaging device according to one embodiment of the present invention.

FIG. 9 illustrates a filtering module according to one embodiment of the present invention. Light that is scattered by the sample is focused onto a filtering module 200, which includes a Rayleigh rejection filter 202. Dichroic mirrors 204 and 206 divert a portion of the scattered light toward fixed filters 208 and 210, which are transmissive over two different spectral windows. The light transmitted by the filters 208 and 210 is detected by imaging detectors 212 and 214, which may comprise a CCD, a CID, an infrared array detector, or the like. The filtering module 200 can be used to produce a sample image for two or more different spectral windows without mechanical motion or spectral scanning (as is required for tunable filters). A signal processor (not shown) may be used, for example, to provide a Raman image, which is corrected for background fluorescence, self absorption, scattering artifacts, spectral or physiological variables, or the like.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An article for measuring at least one parameter of a biological sample comprising:
   (a) at least one source of light capable of irradiating said sample with substantially monochromatic light;
   (b) a filtering module for filtering light inelastically scattered by said sample, said filtering module comprising at least one bandpass filter, said at least one bandpass filter capable of transmitting at least two different spectral windows; and
   (c) at least one detector, wherein said filtering module is capable of selecting two or more spectral windows without requiring mechanical motion.

2. The article of claim 1, wherein said filtering module has a spectral resolution no greater than about 7 cm$^{-1}$ spectral bandpass.

3. The article of claim 1, wherein said filtering module has a transmissivity of at least about 20%.

4. The article of claim 1, wherein said filtering module has a transmissivity of at least about 50%.

5. The article of claim 1, wherein said filtering module has a transmissivity of at least about 80%.

6. An article for measuring at least one parameter of a biological sample comprising:
   (a) at least one source of light capable of irradiating said sample with substantially monochromatic light;
   (b) a filtering module for filtering light inelastically scattered by said sample, said filtering module comprising at least one bandpass filter, said at least one bandpass filter capable of transmitting at least two different spectral windows; and
   (c) at least one detector, wherein said filtering module is capable of selecting two or more spectral windows simultaneously.

7. The article of claim 6, wherein said filtering module has a spectral resolution no greater than about 7 cm$^{-1}$ spectral bandpass.

8. The article of claim 6, wherein said filtering module has a transmissivity of at least about 20%.

9. The article of claim 6, wherein said filtering module has a transmissivity of at least about 50%.

10. The article of claim 6, wherein said filtering module has a transmissivity of at least about 80%.

11. An article for non-invasive determination of concentration of an analyte in a body part comprising:
    (a) at least one source of light capable of irradiating said body part with substantially monochromatic light;
    (b) optics to route the light from said at least one source of light to said body part;
    (c) optics to collect light scattered from said body part;
    (d) a filtering module for filtering light inelastically scattered by said body part, said filtering module comprising at least one bandpass filter, said at least one bandpass filter capable of transmitting at least two different spectral windows;
    (e) at least one detector capable of receiving a signal from said filtering module; and
    (f) means for determining the concentration of the analyte from the intensity of said signal received by said detector, wherein said filtering module comprises a beam splitter, wherein said filtering module is capable of separating the light scattered by said body part into two or more wavelength regions.

12. The article of claim 11, wherein said filtering module comprises at least two filters.

13. The article of claim 11, wherein said filtering module comprises a Rayleigh rejection filter and at least one bandpass filter.

14. The article of claim 11, further comprising a fixture for holding said body part.

15. The article of claim 11, wherein said analyte is glucose.

16. The article of claim 11, wherein said analyte is hemoglobin.

17. The article of claim 11, comprising at least two sources of light for irradiating said body part, each of said two sources of light using substantially monochromatic light of differing wavelengths.

18. An article for non-invasive determination of concentration of an analyte in a body part comprising:
   (a) at least one source of light capable of irradiating said body part with substantially monochromatic light;
   (b) optics to route the light from said at least one source of light to said body part;
   (c) optics to collect light scattered from said body part;
   (d) a filtering module for filtering light inelastically scattered by said body part, said filtering module comprising at least one bandpass filter, said at least one bandpass filter capable of transmitting at least two different spectral windows;
   (e) at least one detector capable of receiving a signal from said filtering module; and
   (f) means for determining the concentration of the analyte from the intensity of said signal received by said detector, wherein said filtering module comprises a dichroic mirror, wherein said filtering module is capable of separating the light scattered by said body part into two or more wavelength regions.

19. The article of claim 18, wherein said filtering module comprises at least two filters.

20. The article of claim 18, wherein said filtering module comprises a Rayleigh rejection filter and at least one bandpass filter.

21. The article of claim 18, further comprising a fixture for holding said body part.

22. The article of claim 18, wherein said analyte is glucose.

23. The article of claim 18, wherein said analyte is hemoglobin.

24. The article of claim 18, comprising at least two sources of light for irradiating said body part, each of said two sources of light using substantially monochromatic light of differing wavelengths.

25. An article for non-invasive determination of concentration of an analyte in a body part comprising:
   (a) at least one source of light capable of irradiating said body part with substantially monochromatic light;
   (b) optics to route the light from said at least one source of light to said body part;
   (c) optics to collect light scattered from said body part;
   (d) a filtering module for filtering light inelastically scattered by said body part, said filtering module comprising at least one bandpass filter, said at least one bandpass filter capable of transmitting at least two different spectral windows;
   (e) at least one detector capable of receiving a signal from said filtering module; and
   (f) means for determining the concentration of the analyte from the intensity of said signal received by said detector, wherein there is at least one detector for each wavelength region, wherein said filtering module is capable of separating the light scattered by said body part into two or more wavelength regions.

26. The article of claim 25, wherein said filtering module comprises at least two filters.

27. The article of claim 25, wherein said filtering module comprises a Rayleigh rejection filter and at least one bandpass filter.

28. The article of claim 25, further comprising a fixture for holding said body part.

29. The article of claim 25, wherein said analyte is glucose.

30. The article of claim 25, wherein said analyte is hemoglobin.

31. The article of claim 25, comprising at least two sources of light for irradiating said body part, each of said two sources of light using substantially monochromatic light of differing wavelengths.

32. A method for the non-invasive determination of concentration of an analyte in a body part comprising the steps of:
   (a) irradiating the body part with light from at least one source of light employing substantially monochromatic light;
   (b) collecting light inelastically scattered from said body part;
   (c) filtering the light scattered by said body part by means of a filtering module comprising at least one bandpass filter, said at least one bandpass filter capable of transmitting at least two different spectral windows;
   (d) detecting the light filtered by said filtering module with at least one detector capable of receiving a signal form said filtering module; and
   (e) calculating the concentration of the analyte from the intensity of said signal received by said detector, wherein said filtering module comprises a beam splitter, wherein said filtering module is capable of separating the light scattered by said body part into two or more wavelength regions.

33. The method of claim 23, wherein said filtering module comprises at least two filters.

34. The method of claim 32, wherein said body part is held in a fixture.

35. The method of claim 32, wherein said analyte is glucose.

36. The method of claim 32, wherein said analyte is hemoglobin.

37. The method of claim 32, wherein the body part is irradiated with light from at least two sources of light, each of said at least two sources of light being substantially monochromatic light having different wavelengths.

38. A method for the non-invasive determination of concentration of an analyte in a body part comprising the steps of:
   (a) irradiating the body part with light from at least one source of light employing substantially monochromatic light;
   (b) collecting light inelastically scattered from said body part;
   (c) filtering the light scattered by said body part by means of a filtering module comprising at least one bandpass filter, said at least one bandpass filter capable of transmitting at least two different spectral windows;
   (d) detecting the light filtered by said filtering module with at least one detector capable of receiving a signal form said filtering module; and
   (e) calculating the concentration of the analyte from the intensity of said signal received by said detector, wherein said filtering module comprises a dichroic mirror wherein, said filtering module is capable of separating the light scattered by said body part into two or more wavelength regions.

39. The method of claim 38, wherein said filtering module comprises at least two filters.

40. The method of claim 38, wherein said body part is held in a fixture.

41. The method of claim 38, wherein said analyte is glucose.

42. The method of claim 38, wherein said analyte is hemoglobin.

43. The method of claim 38, wherein the body part is irradiated with light from at least two sources of light, each of said at least two sources of light being substantially monochromatic light having different wavelengths.

44. A method for the non-invasive determination of concentration of an analyte in a body part comprising the steps of:

(a) irradiating the body part with light from at least one source of light employing substantially monochromatic light;

(b) collecting light inelastically scattered from said body part;

(c) filtering the light scattered by said body part by means of a filtering module comprising at least one bandpass filter, said at least one bandpass filter capable of transmitting at least two different spectral windows;

(d) detecting the light filtered by said filtering module with at least one detector capable of receiving a signal form said filtering module; and (e) calculating the concentration of the analyte from the intensity of said signal received by said detector, wherein there is one detector for each wavelength region, wherein said filtering module is capable of separating the light scattered by said body part into two or more wavelength regions.

45. The method of claim 44, wherein said filtering module comprises at least two filters.

46. The method of claim 44, wherein said body part is held in a fixture.

47. The method of claim 44, wherein said analyte is glucose.

48. The method of claim 44, wherein said analyte is hemoglobin.

49. The method of claim 25, wherein the body part is irradiated with light from at least two sources of light, each of said at least two sources of light being substantially monochromatic light having different wavelengths.

50. An article for non-invasive determination of concentration of an analyte in a body part comprising:

(a) a source of light for irradiating said body part with substantially monochromatic light;

(b) a filtering module for filtering light inelastically scattered by said body part, said filtering module comprising at least one bandpass filter, said at least one bandpass filter capable of transmitting at least two different spectral windows; and (c) at least one detector, wherein said filtering module is capable of selecting two or more spectral windows without requiring mechanical motion.

51. An article for non-invasive determination of concentration of an analyte in a body part comprising:

(a) a source of light for irradiating said body part with substantially monochromatic light;

(b) a filtering module for filtering light inelastically scattered by said body part, said filtering module comprising at least one bandpass filter, said at least one bandpass filter capable of transmitting at least two different spectral windows; and (c) at least one detector, wherein said filtering module is capable of selecting two or more spectral windows simultaneously.

* * * * *